United States Patent [19]

Girardeau et al.

[11] Patent Number: 4,912,245

[45] Date of Patent: Mar. 27, 1990

[54] PHOSPHORIC ACID ESTER-BASED COMPOSITIONS, PROCESS FOR THE PREPARATION THEREOF

[75] Inventors: Yvette Girardeau, Fontains/Sur/Saone; Christian Segaud, Aulnay/Sous/Bois, both of France

[73] Assignee: Rhone-Poulenc Chimie, Courbevoie Cedex, France

[21] Appl. No.: 62,628

[22] Filed: Jun. 16, 1987

[30] Foreign Application Priority Data

Jul. 11, 1986 [FR] France ................. 86 10159

[51] Int. Cl.$^4$ .............................................. C07F 9/09
[52] U.S. Cl. ................................... 558/113; 558/186; 252/174.16
[58] Field of Search ..................... 558/113, 186; 252/174.16

[56] References Cited

U.S. PATENT DOCUMENTS

| | | | |
|---|---|---|---|
| 3,004,056 | 10/1961 | Nunn, Jr. et al. | 558/186 |
| 3,004,057 | 10/1961 | Nunn, Jr. et al. | 558/186 |
| 3,117,152 | 1/1964 | Michaels | 558/186 |
| 3,317,305 | 5/1967 | Stefcik et al. | 71/3 |
| 3,422,166 | 1/1969 | Davis | 558/186 |
| 3,755,509 | 8/1973 | Nunn, Jr. et al. | 558/186 |

FOREIGN PATENT DOCUMENTS

| | | |
|---|---|---|
| 0077233 | 9/1982 | European Pat. Off. . |
| 3210869A1 | 10/1982 | Fed. Rep. of Germany . |
| 3302648 | 8/1984 | Fed. Rep. of Germany . |
| 2394602 | 1/1979 | France . |
| 2157952A | 11/0685 | United Kingdom . |
| 918430 | 2/1963 | United Kingdom . |
| 2105745A | 3/1983 | United Kingdom . |
| 2115284 | 9/1983 | United Kingdom . |
| 2115284A | 9/1983 | United Kingdom . |

*Primary Examiner*—Anton H. Sutto
*Attorney, Agent, or Firm*—Finnegan, Henderson, Farabow, Garrett and Dunner

[57] ABSTRACT

Surfactant compositions in an acidic or neutralized form containing a mixture of at least one polyoxyalkylenated phosphoric acid monoester and at least one polyoxyalkylenated diester and a nonionic polyoxyalkylenated compound wherein the phosphoric acid diester:phosphoric acid monoester molar ratio before neutralization, if carried out, is at least equal to 0.9:1 and the phosphoric acid monoester and phosphoric acid diester content is at least 1 mol %, preferably at least 50 mol % of said composition. The surfactant compositions are prepared by phosphatization of a nonionic polyoxyalkylenated compound at a temperature of from about 35° to about 45° C. followed by maturing at from about 40° to about 60° C., in a stirred turbulent state. The compositions are useful in the formulation of active substances in the form of microgranules and flowables.

9 Claims, No Drawings

PHOSPHORIC ACID ESTER-BASED COMPOSITIONS, PROCESS FOR THE PREPARATION THEREOF

The present invention relates to new surfactant compositions. More particularly, he present invention relates to new surfactant compositions which are prepared from phosphoric acid esters of polyoxyalkylenated compounds which are in acidic or neutralized form. The present invention also relates to a process for the preparation of the surfactant compositions and to the use thereof in the formulation of active substances. More particularly, the surfactant compositions are useful in the form of aqueous suspensions called "flowables" which are diluted upon use or in the form of granules which are placed into suspension upon use.

It is known to use surfactant compositions which are prepared from phosphoric acid esters of polyoxyalkylenated compounds for the preparation of water suspensions of insoluble substances.

It is also known to prepare biocidal compositions which can be dispersed in water from surfactants of polyoxyethylenated tristyrylphenolphosphoric acid monoester and diester, or the salts thereof and, if appropriate, nonionic surfactants of polyglycol ether. (German Patent No. 3,302,648).

It is also known to form herbicidal mixtures wherein the active component of the composition consists of an anionic surfactant from the series of the mono- or di-phosphoric acid esters of phenol polyglycolethers and a non-ionic surfactant from the series of the alkoxy, alkanoyloxy or phenol polyglycol ethers which differ by at least one glycol unit. (British Patent Application No. 2,115,284)

The phosphoric acid esters from mixtures of phosphoric acid monoesters and diesters, in the acid or the neutralized form are also used in SOPROPHOR 3D 33 or SOPROPHOR FL which are marketed by Rhone-Poulenc. In these products the proportion of monoester groups is predominant as compared to the diester groups.

A main object of the present invention is to provide compositions with particularly useful wettability and dispersability properties having a phosphoric acid monoester and diester surfactant mixture containing an adequate proportion of diester groups.

To achieve the objects and in accordance with the purpose of the invention, as embodied and broadly described herein the invention comprises a surfactant composition comprising a mixture of at least one phosphoric acid monoester of a polyoxyalkyenated compound of formula I and at least one phosphoric acid diester of a polyoxyalkylenated compound of formula II:

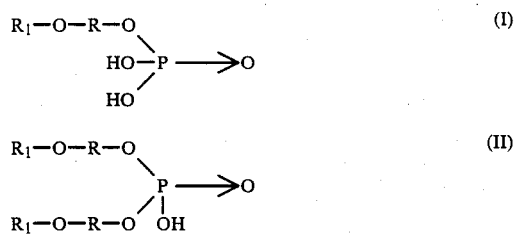

wherein each O-R is from 1 to 80 identical or different $C_2$-$C_4$ oxyalkylenated units and each $R_1$ is a straight-chain or branched $C_8$-$C_{20}$ alkyl or alkenyl radical or a aryl radical of the formula (III):

wherein m is an integer from 1 to 3 inclusive; p is an integer from 1 to 2 inclusive; each $R_3$ is a hydrogen atom or a $C_1$-$C_4$ alkyl radical; and each $R_2$ is a $C_4$-$C_{12}$, preferably $C_8$-$C_9$, alkyl radical or a radical of formula (IV)

wherein $R_4$ is a hydrogen atom, a $C_1$-$C_4$ alkyl radical or a phenyl radical wherein each $R_1$ in the formula II can be identical or different. The molar ratio of the phosphoric acid diester or diesters of the formula II to the phosphoric acid monoester or monoesters of formula I is greater than or equal to 0.9:1, preferably from 0.9:1 to 7:1 and the molar content of the monoester or monoesters and diester or diesters is at least 1 mol percent, preferably at least 50 mol percent, of the surfactant composition. The composition further comprises at least one polyoxyalkylenated compound of the formula V:

$$R'_1-O-R'-OH \qquad (V)$$

wherein $R'_1$ is a straight chain or branched $C_8$-$C_{20}$ alkyl or alkenyl radical or an aryl radical of formula (III) and O—R' is a $C_2$-$C_4$ oxyalkylenated unit. Preferably, $R'_1$ and O-R' are identical to $R_1$ and O-R.

Preferably phosphoric acid monoesters and the phosphoric acid diesters are employed which contain from 3 to 60 oxyalkylenated O—R units, each $R_1$ is selected from the group consisting of tri(1-phenylethyl)phenyl, di(1-phenylethyl)phenyl, nonylphenyl, octylphenyl, dodecylphenyl, tridecylphenyl, octadecyl and octadecenyl radicals, and each R is an ethylene or propylene radical.

Exemplary phosphoric acid esters of the formulas I and II include phosphoric acid monoesters and diesters of polyoxyethylenated tri(1-phenylethyl)phenols which contain from 0 to 40 moles of ethylene oxide per mole of phenol; phosphoric acid monoesters and diesters of polyoxyethylenated di(1-phenylethyl)phenols which contain from 3 to 20 moles of ethylene oxide per mole of phenol; phosphoric acid monoesters and diesters of polyoxyethylenated nonylphenols or octylphenols which contain from 5 to 40 moles of ethylene oxide per mole of phenol; phosphoric acid monoesters and diesters of polyoxyethylenated $C_{13}$ oxoalcohol which contain from 3 to 20 moles of ethylene oxide per mole of alcohol; phosphoric acid monoesters and diesters of polyoxyethylenated and polyoxypropylenated tri(1-phenylethyl)phenols which contain from 5 to 40 moles of ethylene oxide and from 5 to 40 moles of propylene oxide distributed randomly or in blocks; and phosphoric acid monoesters and diesters of polyoxyethylenated or polyoxypropylenated di(1-phenylethyl)phenols which contain from 5 to 40 moles of ethylene oxide and from 5 to 40 moles of propylene oxide which are distributed randomly or in blocks.

Preferably, polyoxyalkylenated derivatives of the formula V are employed which contain from 3 to 60 oxyalkylenated O—R units and wherein $R'_1$ is selected from the group consisting of tri(1-phenylethyl)phenyl, di(1-phenyletyl)phenyl, nonylphenyl, octylphenyl, dodecylphenyl, tridecyl, octadecyl or octadecenyl radicals, and R is an ethylene and/or propylene radical Exemplary polyoxyalkenylated compounds include polyoxyethylenated tri(1-phenyletyl)phenol which contains from 10 to 40 moles of ethylene oxide per mole of phenol, polyoxyethylenated di(1-phenylethyl)phenol which contains from 3 to 20 moles of ethylene oxide per mole of phenol, polyoxyethylenated nonylphenol or octylphenol which contains from 5 to 40 moles of ethylene oxide per mole of phenol, polyoxyethylenated $C_{13}$ oxoalcohol which contains from 3 to 20 moles of ethylene oxide per mole of alcohol, polyoxyethylenated an polyoxypropylenated tri(1-phenylethyl)phenol which contains from 5 to 40 moles of ethylene oxide and from 5 to 40 moles of propylene oxide which is distributed randomly or in blocks and polyoxyethylenated and polyoxypropylenated di(1-phenylethyl)phenol which contains from 5 to 40 moles of ethylene oxide and from 5 to 40 moles of propylene oxide which is distributed randomly or in blocks The surfactant compositions of the present invention may be prepared by mixing compounds I, II and V, in the quantities as set forth above, at a temperature sufficient to achieve a homogeneous mixture. This procedure is particularly employed when $R'_1$ and O—R' are not identical to $R_1$ and O—R.

Preferably the surfactant compositions re prepared by the phosphatization of at least one polyoxyalkylenated compound of the formula $R_1$—OR—OH with phosphorus pentoxide. The process for preparing the polyoxyalkylenated compounds of the formula V is carried out in two stages and comprises the steps of:
(1) an actual phosphatization stage, carried out by continuously introducing phosphorus pentoxide into a turbulently stirred medium consisting of said polyoxyalkylenated compound containing water in a quantity sufficient to initiate the phosphatization reaction. The temperature at the beginning of the reaction is of the order of from about 35 to about 40° C, said temperature being maintained at a temperature less than or equal to 45° C. until the introduction of phosphorus pentoxide is complete, the total quantity of phosphorus pentoxide employed corresponding to a polyoxyethylenated compound to $P_2O_5$ molar ratio equal to $3\pm0.3:1$, and
(2) maturing the reaction mixture while turbulently stirring at a temperature of from about 40 to about 60° C.

Preferably the medium contains water in an amount of from about 0.0025 to 0.05 mole per mole of the polyoxyalkylenated compound. This quantity of water is sufficient to initiate the phosphatization reaction. The water formed during the reaction is sufficient to maintain the reaction.

The temperature maintained during Step (1) of the process must be sufficient to produce a medium of sufficiently low viscosity such that it may be subjected to turbulent stirring but should not exceed 45° C. The temperature during the maturing stage must be maintained between 40 and 60° C. These two conditions are necessary to obtain a mixture wherein the molar ratio of the phosphoric acid diester or diesters to the phosphoric acid monoester or monoesters is greater than or equal to 0.9:1.

Preferably, step 1 of the process may be carried out at atmospheric pressure for from 1 to 6 hours. Step 2 of the process may preferably be carried out for from 30 minutes to 2 hours.

The present invention also relates to the surfactant compositions which are obtained by neutralizing the acidic groups of the surfactant compositions containing at least one phosphoric acid monoester of formula I and phosphoric aid diester of the formula II.

The neutralization of the acidic groups of the surfactant compositions may be carried out by using a base in a quantity sufficient to obtain a composition which has a pH of at least 7, preferably from 7.5 to 8. Exemplary bases which may be employed include alkali metal hydroxides, such as sodium hydroxide and potassium hydroxide and amines such as diethanolamine, triethanolamine, morpholine, and N-methylcyclohexylamine.

The neutralization reaction is exothermic and is carried out with turbulent stirring at a temperature such that the temperature of the medium does not exceed 60° C. On an industrial scale this reaction is carried out at a temperature of about 45° C for a duration of from about 15 to 45 minutes.

The surfactant compositions of the present invention are particularly well suited for the formulation of active substances which are insoluble or sparingly soluble in water at ambient temperatures, such as from 15° to 25° C, thus requiring them to be in suspension when applied. The term "sparingly soluble" refers to a solubility of less than 1% by weight.

Exemplary active substances which can be formulated according to the present invention include pigments and carriers, colorants, optical whiteners and various additives in different industries such as plastics, paints, textile, concrete, cosmetics, and pharmaceuticals.

The surfactant compositions obtained in accordance with the process of the present invention are preferably used in agricultural chemicals. More particularly, the surfactant compositions are useful in the formulation of active substances such as insecticides, acaricides, fungicides and various combinations thereof, herbicides, nematicides, molluscicides, atractants, repellents and rodenticides.

Exemplary types of insecticides which may be formulated according to the present invention include organohalogen or chlorinated compounds; carbinols; organophosphorus compounds; sulfones and sulfonates; carbamates; benzylureas; and synthetic pyrethrinoids.

Exemplary fungicides which may be formulated according to the present invention include carbamates; benzene derivatives; phenol derivatives; quinones; dicarboximides; amines and amides; diazines; sulfamides and sulfur derivatives; guanidines; heterocyclic compounds; monoethyl metal phosphites; and organotins.

Herbicides which may be formulated according to the process of the present invention include phenolic compounds; carbamates; substituted ureas; diazines; triazines; amides; quaternary ammonium compounds; benzonitriles; toluidines; and triazoles.

On or more active substances which belong to the same class of biocides or to a different class may be formulated.

The surfactant compositions of the present invention may be used to formulate active substances in the form of microgranules.

If the active substance is in the liquid form, a pulverulent support such as calcium silicates and precipitated silicas with high absorption capacity (for example ZEOSIL 39 A of Rhone-Poulenc) can be used in a quantity sufficient to absorb the active substance to obtain a dry powder.

Preferably microgranules produced according to the present invention comprise:
 from 10 to 95% by weight of at least one active substance;
 from 3 to 10% by weight of the surfactant compositions of the invention and, if required, one or more anionic or nonionic surfactant(s) which are commonly used in this type of application;
 from 2 to 10% by weight of binding agent;
 from 0 to 5% by weight of wetting agent, if required;
 from 0 to 75% by weight of filler, if required;
 from 0 to 5% by weight of disintegrating agent, if required; and
 auxiliary products, if required Exemplary binding agents employed in microgranules produced according to the process of the present invention include copolymers obtained from an unsaturated carboxylic acid and an α-olefin compound and/or a vinyl compound such as maleic anhydride/diisobutylene copolymers which are sold by Rhone-Poulenc or Geronazzo under the trade names SOPROPON T 36, SOPROTON T 36 K or GEROPON TA 72; copolymers with carboxyl groups such as polyacrylic acids which are sold by Rhone-Poulenc under the name DISPERSANT DG or DA; and polynaphthalenesulfonates and polyalkylnaphthalenesulfonates which are sold by Rone-Poulenc under the name SUPRAGIL NS 90 or MNS 90 or by Geronazzo under the name GEROPON RM 210.

Exemplary anionic or nonionic surfactants which may be employed in addition to the surfactant composition of the present invention include polyoxyethylenated and/or polyoxypropylenated derivatives of aliphatic alcohols and fatty amides which may, if required, be polyoxyethylenated.

Exemplary wetting agents which may be employed, if required, include soaps of alkali metals such as sodium or potassium salts of saturated or unsaturated $C_8$-$C_{24}$ fatty acids, sodium N-lauryl sarcosinate and sodium N-acyl sarcosinate; alkali metal sulfonates such as sodium diethylhexylsulfosuccinate; alkylbenzenesulfonates such as nonyl- or dodecylbenzenesulfonates of sodium, diethanolamine, triethanolamine; N-methylcyclohexylamine; alkali metal alkylnaphthalenesulfonates and alkali metal N-alkyl laurates; sulfates and sulfated products such as sodium lauryl sulfate; polyoxyethylenated and sulfated fatty alcohols; and polyoxyethylenated and sulfated alkylphenols.

Exemplary fillers which may be employed, if required include ground natural inert compounds such as kaolin, attapulgite, bentonite, chalk, talc or synthetic products such as precipitated silica, pyrogenic silica, and calcium carbonate.

Disintegrating agents serve to assist in the release of the active substance. Exemplary disintegrating substances which may be employed include bentonite, corn starch or highly soluble inorganic salts such as sodium bicarbonate or sodium chloride.

The auxiliary products, f required, are selected from the group consisting of antifoaming agents such as polysiloxane; anticaking agents such as precipitated silica; antistatic agents such as lithium chloride and the potassium salt of tridecylphosphoric acid; agents which protect against oxidation, UV radiation and pH variations; and miscellaneous additives such as colorants or adjuvants intended for modifying the adherence of the treatment mixture to the plant.

The microgranules may be prepared according to known granulation or agglomeration methods, such as in a fluidized bed, by atomization if the melting point of the active substance permits, on a rotating plate, or by extrusion.

The microgranules may vary ih size from about 100 to about 500 microns or from about 0.1 to about 2 mm, depending on the granulation method employed.

The microgranules have very good dispersibility in water, good resistance to handling without forming dust, high active substance content, good physicochemical stability, and good flowability.

Another particularly useful application for the surfactant composition of the present invention is in the formulation of at least one solid active substance in the form of fluid aqueous dispersions called "flowables". The active substance must have a melting point greater than 65° C, preferably greater than 100° C, and must not be sensitive to hydrolysis.

Preferably, the fluid aqueous dispersions comprise:
 from 10 to 89% by weight of water;
 from 10 to 65% of at least one solid active substance;
 from 0.2 to 20% of the surfactant composition of the present invention and one or more other anionic or nonionic surfactant(s) commonly used in this type of application;
 from 0.8 to 20% of at least one antifreeze;
 from 0 to 10% of wetting agent, if required;
 from 0 to 5% of thickener, if required; and miscellaneous adjuvants.

The surfactant composition of the present invention has a wetting capacity and thus the presence of a wetting agent is not absolutely essential. However, if the presence of such an aqent is desired, the latter may be chosen from amongst those already mentioned above.

Antifreezes prevent possible crystal formation during storage of the dispersions. Conventional antifreezes such as ethylene glycol, propylene glycol, glycerol, diethylene glycol, triethylene glycol, tetraethylene glycol, and urea may be used.

Thickeners are preferably employed to maintain the active substance in suspension and prevent any sedimentation during storage. Organic thickeners which are water-soluble or capable of swelling in water, such as polysaccharides of the xanthan gum type, alginates, carboxylated or hydroxylated methylcelluloses, synthetic macromolecules such as polyacrylates, polymaleates, polyvinyppyrrolidones, polyethylene glycols, polyvinylalcohols, or inorganic thickeners such as bentonites and silicas may be used.

Exemplary auxiliary additives which may be employed include antifoaming agents such as polysiloxanes, protective agents against oxidation, UV radiation and pH variation, colorants, bactericides and adjuvants intended for modifying the adherence of the treatment mixture to the plant.

The aqueous dispersions may be prepared by a known process such as, for example, by dissolving the surfactant composition in antifreeze and water to form an aqueous dispersion, stirring and then grinding the dispersion until a particle size of from 1 to 10 microns is obtained; degassing the dispersion and adjusting the viscosity of the dispersion by adding a thickener and water while gently stirring, to obtain the desired concentration and a viscosity of the order of 20 to 60 s, measured with Ford Cup No. 4.

The dispersions are stable during storage; have a high active substance content, a low viscosity, an good stability during the period of application and are stable when diluted with water to the usage dose.

The present invention will be described more completely with the aid of the following examples, which are merely representative and do not serve to limit the scope of the invention.

EXAMPLE 1

Preparation of the Surfactant Compositions In the Acid Form 3 moles of the polyoxyalkylenated derivative of the formula $R_1$—OR—OH (formula V) were charged into a reactor equipped with a turbulent state propeller stirring system, a cooling system and a heating system.

The temperature was raised to 37° C. and 1 mole of $P_2O_5$ was introduced at a constant rate, with turbulent stirring over a period of about 1 hour, 15 minutes. The temperature of the medium was maintained at 43° C.±1° C. by cooling, until the introduction of the $P_2O_5$ was complete.

Upon completion of the addition of $P_2O_5$, the reaction was allowed to proceed at the same temperature for 30 minutes with stirring (maturing stage).

The product obtained was analyzed by potentiometry to determine the diester, monoester and fee phosphoric acid content.

In Tables I and II, the diester:monoester ratio are referred to as "II/I" and the total quantity of diester and monoester are referred to as "II +I".

The content of the polyoxyalkylenated derivative of the formula V present in the product obtained is referred to as "% nonionic."

EXAMPLE 2

Preparation of the Surfactant Compositions Which Are Neutralized With Triethanolamine or Potassium Hydroxide The product obtained in Example 1 was neutralized with triethanolamine or with 38% potassium hydroxide until a pH of the medium of approximately 8 was obtained. During neutralization the cooling was controlled so that the temperature did not exceed 45° C.

In the Tables, "II/I" will refer to the molar ratio of the diester to the monoester in the acid form, i.e., before neutralization.

This also applies to the term "II +I".

The following example is directed to the preparation of a fluid aqueous dispersion hereafter referred to as a "flowable".

EXAMPLE 3

Preparation of a "Flowable"

6 g of the surfactant composition of the present invention were dissolved in 19.5 g of monoethylene glycol and 0.3 g of antifoam 416/R, manufactured by Rhone-Poulenc, 115.2 g of water were then added. 135 g of the active substance were added slowly, with stirring. The stirring was maintained for approximately 3 minutes to obtain a homogeneous mixture.

A predispersion was obtained which was then ground in a "mini motor mill" marketed by Eiger Engineering Ltd. The grinding chamber was filled with 59 g of 1 mm-diameter glass beads and the rotation speed was 4,000 rpm. The grinding was carried out for approximately 4 minutes to obtain particles having a diameter between 2 and 6 microns.

The mixture obtained was allowed to stand for from 3 to 4 hours to remove air bubbles and the foam which were present.

The viscosity of the "flowable" obtained was adjusted by adding 24 g of a 2% solution in water of RHODOPOL 23 which is manufactured by Rhone-Poulenc.

The "flowable" obtained was tested for particle size distribution using a "Coulter Counter TA II" which is marketed by Coultronics A consistency determination was made using a Ford Cup No. 4, and a rheological test and a determination of the apparent viscosity at a velocity gradient of 77.112 $s^{-1}$ were performed with a Rheomat 30 made by Contraves, both before adding RHODO POL 23 and after adding RHODOPOL 23.

In Tables I and II "RHODOPOL 23" refers to the percentage by weight of the flowable in the 2% RHODOPOL 23 solution; 0 refers to the mean diameter after grinding; and v$CF_4$ refers to the consistency determined with a Ford Cup No. 4.

EXAMPLE 4

A "flowable" was prepared according to the procedure set forth in Example 3 containing as an active substance, plictran (tricyclohexylhydroxy stannate) and a surfactant composition prepared according to the procedure of Example 1 from polyoxyethylenated tri(1-phenylethyl)phenol containing 16 moles of ethylene oxide per mole of phenol.

This surfactant composition had a molar ratio of diester:monoester of 5.53:1 a total molar quantity of diester and monoester of 94.6%; and a free phosphoric acid content of 4.1 mol%.

The properties of the "flowable" obtained are set forth in Table 1.

COMPARATIVE EXAMPLE 5

A "flowable" was prepared according to the procedure set forth in Example 3 containing as an active substance, plictran, a surfactant composition which was prepared by phosphatizing polyoxyethylenated tri(1-phenylethyl)phenol containing 16 moles of ethylene oxide per mole of phenol with $P_2O_5$, as set forth in the procedure of Example 1, except that the maturing stage was carried out for 1 hour at 90±2° C. instead of for 30 minutes at 43±1° C.

This composition contained a molar ratio of diester:monoester of 011:1; a total molar quantity of diester and monoester of 25.5%; and a free phosphoric acid content of 18 mol%.

The properties of the "flowable" obtained are set forth in Table I.

EXAMPLE 6

A "flowable" was prepared according to the procedure set forth in Example 3 which contained as an active substance, diuron (dichlorophenyldimethylurea), and 1% by weight of a surfactant composition prepared according to Example 1 using polyoxyethylenated nonylphenol containing 6 moles of ethylene oxide per mole of phenol.

The surfactant composition had a molar ratio of diester:monoester of 2.13:1; a total molar quantity of the diester and monoester of 90.22%; and a free phosphoric acid content of 2.55 mol%.

The quantity of water present in the "flowable" was 118.2 g rather than 115.2 g as in Example 3.

The properties of the "flowable" obtained are set forth in Table I.

COMPARATIVE EXAMPLE 7

A "flowable" was prepared according to the procedure of Example 3 which contained as an active substance, diuron, and 2% by weight of a surfactant composition prepared by phosphatizing polyoxyethylenated nonylphenol containing 6 moles of ethylene oxide per mole of phenol with $P_2O_5$, according to the procedure of Example 1, except that the maturing stage was carried out at 90° C. for 1 hour.

The surfactant composition had a molar ratio of diester:monoester of 0.7:1; a total molar quantity of the diester and monoester of 63.25%; and a free phosphoric acid content of 10.2 mol%.

The properties of the "flowable" obtained are set forth in Table I.

It is not possible to prepare a "flowable" with 1% by weight of the surfactant composition because it is not possible to grind the surfactant composition because of its insufficient dispersing capacity.

EXAMPLE 8

A "flowable" was prepared according to the procedure of Example 3 which contained as an active substance, carbofuran (2,3-dihydro-2,2-dimethyl-7-benzofuranyl methylcarbamate) and a surfactant composition prepared by neutralizing a surfactant composition identical to that employed in Example 4 (i.e. derived from polyoxyethylenated (tri(1-phenylethyl)phenol containing 16 moles of ethylene oxide per mole of phenol) with potassium hydroxide according to the procedure described in Example 2.

Before neutralization, the surfactant composition had a molar ratio of diester:monoester of 5.53:1, a total molar quantity of the diester and monoester of 94.6%, and a free phosphoric acid content of 4.1 mol%.

The properties of the "flowable" obtained are set forth in Table II.

EXAMPLE 9

A "flowable" was prepared according to the procedure of Example 3 which contained as an active substance, carbaryl (naphthyl N-methylcarbamate), and a surfactant composition obtained by neutralizing a surfactant composition identical to that employed in Example 6 (i.e. derived from polyoxyethylenated nonylphenol containing 6 moles of ethylene oxide per mole of phenol) with potassium hydroxide according to the procedure described in Example 2.

Before neutralization, the surfactant composition and a molar ratio of diester:monoester of 2.13:1, a total molar quantity of the diester and monoester of 90.22%, and a free phosphoric acid content of 2.55 mol%.

The properties of the "flowable" obtained are set forth in Table II.

EXAMPLE 10

A "flowable" was prepared according to the procedure of Example 3 which contained as an active substance, simazine (chlorobis(ethylamino)-s-trizzine), and a surfactant composition obtained by neutralizing a surfactant composition prepared according to the procedure of Example 1 using polyoxyethylenated nonylphenol containing 9 moles of ethylene oxide per mole of phenol with potassium hydroxide according to the procedure described in Example 2.

Before neutralization, the surfactant composition had a molar ratio of diester:monoester of 1.20:1, a total molar quantity of diester and monoester of 82.2%, and a free phosphoric acid content of 1.9 mol%.

The properties of the "flowable" obtained are set forth in Table II.

EXAMPLE 11

A surfactant composition was prepared by carrying out a phosphatization operation according to the procedure of Example 1 using polyoxyethylenated tri(1-phenylethyl)phenol containing 16 moles of ethylene oxide pr mole of phenol.

The maturing operation was carried out for 1 hour at 60° C.

The surfactant composition had a molar ratio of diester:monoester of 0.9:1, and a total molar quantity of diester and monoester of 54.9%.

The composition was neutralized with triethanolamine according to the procedure set forth in Example 2.

PREPARATION OF A "FLOWABLE"

30 g of the surfactant composition were dissolved in 80 g of monoethylene glycol. 0.3 g of antifoam 416/R and 392 g of water were added.

500 g of atrazine (chloroethylaminoisopropylamino-s-triazine) were slowly added, with stirring for 15 minutes.

A predispersion was obtained which was then ground in a "Dyno Mill KDL", marketed by Dyno. The grinding chamber having a volume of 1.2 liter, was filled with 1.75 kg of 1 mm glass beads and the rotation speed was 3,350 rpm.

The grinding was carried out twice, for a period of 18 minutes each time, with a flow rate of 8.4 liters/h, to obtain particles having a diameter between 0.5 and 2 microns.

The mixture was allowed to stand for 12 hours.

The properties of the "flowable" obtained are set forth in Table II.

COMPARATIVE EXAMPLE 12

A "flowable" was prepared according to the procedure of Example 11 which contained as an actives substance, atrazine, and a surfactant composition. The surfactant composition was prepared according to the procedure of Example 1 by phosphatizing polyoxyethylenated tri((1-phenylethyl)phenol containing 16 moles of ethylene oxide per mole of phenol. The maturing stage was carried out for 1 hour at 85° C, followed by neutralization with triethanolamine according to the procedure of Example 2.

Before neutralization, the surfactant composition had a molar ratio of diester:monoester of 0.4:1, and a total molar quantity of the diester and monoester of 48.5%.

The properties of the "flowable" obtained are set forth in Tables I and II.

TABLE I

| Example | 4 | | 5 | | 6 | | 7 | |
|---|---|---|---|---|---|---|---|---|
| Active substance | plictran | | plictran | | diuron | | diuron | |
| II/I | 5.53 | | 0.11 | | 2.13 | | 0.7 | |
| II + I | 94.6 | | 25.5 | | 90.22 | | 63.25 | |
| % $H_3PO_4$ | 4.1 | | 18 | | 2.55 | | 10.2 | |
| % nonionic | 1.3 | | 56.5 | | 7.23 | | 26.55 | |
| % surfactant by weight in the flowable | 2 | | 2 | | 1 | | 2 | |
| Rhodopol 23 | 0 | 8 | 0 | 8 | 0 | 8 | 0 | 8 |
| $vCF_4$ in s | 14 | 37 | 17 | 45 | 14 | 25 | 15 | 30 |
| v apparent in mPa s | 17.5 | 106 | 22 | 107 | 6.6 | 73.3 | 28 | 86.3 |
| v Bingham in mPa s | 19 | 32.3 | 28 | 42.2 | 14.3 | 23.6 | 19.6 | 27.9 |
| flow threshold in $s^{-1}$ | 0 | 6.4 | 0 | 6.7 | 0 | 4.1 | 0.18 | 4.9 |
| 0 in micron | 2.9 | | 2.9 | | 3.4 | | 2.9 | |
| median in micron | 1.91 | | 1.80 | | 2.48 | | 2.45 | |
| mode in micron | 1.79 | | 1.79 | | 2.26 | | 2.26 | |

TABLE II

| Example | 8 | | 9 | | 10 | | 11 | 12 |
|---|---|---|---|---|---|---|---|---|
| Active substance | carbofuran | | carbaryl | | simazine | | atrazine | atrazine |
| II/I | 5.53 | | 2.13 | | 1.20 | | 0.9 | 0.4 |
| II + I | 94.6 | | 90.22 | | 82.2 | | 54.9 | 48.5 |
| % $H_3PO_4$ | 4.1 | | 2.55 | | 1.9 | | | |
| % nonionic | 1.3 | | 7.23 | | 15.9 | | | |
| % surfactant by weight in the flowable | 2 | | 2 | | 2 | | 6 | 6 |
| Rhodopol 23 | 0 | 8 | 0 | 8 | 0 | 6* | 0 | 0 |
| $vCF_4$ in s | 14 | 30 | 17 | 39 | 25 | 50 | 18 | 24 |
| v apparent in mPa s | 17.8 | 91.6 | 42.3 | 139 | 120 | 139 | 92 | 222 |
| v Bingham in mPa s | 21.4 | 30.3 | 27.1 | 56.2 | 50 | 55.6 | 1,000 | 1,200 |
| flow threshold in $s^{-1}$ | 0 | 3.5 | 1.2 | 7.71 | 0 | 5.9 | 4.2 | 62 |
| 0 in micron | 3.94 | | 5.08 | | 4.39 | | 1.3 | 1.3 |
| median in micron | 2.99 | | 3.52 | | 2.91 | | | |
| mode in micron | 2.85 | | 2.26 | | 2.85 | | | |

*the quantity of water in the flowable is increased by 2% by weight

What is claimed:

1. A surfactant composition comprising a mixture of (1) at least one phosphoric acid monoester of a polyoxyalkylenated derivative of formula I and (2) at least one phosphoric acid diester of a polyoxyalkylenated compound of formula II

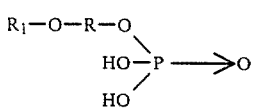 (I)

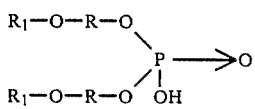 (II)

wherein each O—R is from 1 to 80 identical or different $C_2$-$C_4$ oxyalkylenated units and each $R_1$ is a straight-chain or branched $C_8$-$C_{20}$ alkyl or alkenyl radical or an aryl radical of formula (III):

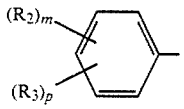 (III)

wherein m is an integer from 1 to 3 inclusive;
p is an integer from 1 to 2 inclusive;
each $R_3$ is a hydrogen atom or a $C_1$-$C_4$ alkyl radical; and
each $R_2$ is a $C_4$-$C_{12}$ alkyl radical or a radical of formula (IV):

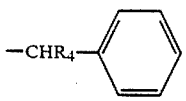 (IV)

wherein $R_4$ is a hydrogen atom or a $C_1$-$C_4$ alkyl radical or a phenyl radical; wherein each $R_1$ in the formula II can be identical of different and wherein the molar ratio of said phosphoric acid diester or diesters of formula II to said phosphoric acid monoester or monoesters of formula I is from about 2.13:1 to about 7.0:1, and the molar content of said monoester or monoesters and said diester or diesters is at least 1 mol% of said surfactant composition, said composition further comprising (3) at least one polyoxyalkylenated compound of formula V:

$$R'_1-O-R'-OH \qquad (V)$$

wherein $R'_1$ is a straight chain or branched $C_8-C_{20}$ alkyl or alkenyl radical or aryl radical of formula (III) and O-R' is a $C_2-C_4$ oxyalkylenated unit.

2. The surfactant composition of claim 1, wherein the molar ratio of said phosphoric acid diester or diesters of formula II to said phosphoric acid monoester or monoesters of formula I is from about 2.13:1 to about 7:1 and said molar content of said monoester or monoesters and said diester or diesters represents at least about 50 mol% of said surfactant composition.

3. The surfactant composition of claim 1, wherein each $R_1$ and $R'_1$ is selected from the group consisting of tri(1-phenylethyl)phenyl, di(1-phenylethyl)phenyl, nonylphenyl, octylphenyl, dodecylphenyl, tridecyl, octadecyl and octadecenyl radicals and wherein each R and R' is selected from the group consisting of an ethylene and a propylene radical, and wherein each O—R and O—R' is from 3 to 60 oxyalkylenated units.

4. A process for preparing the surfactant composition of claim 1 comprising the steps of
(1) phosphatizing by continuously introducing phosphorus pentoxide into a medium subjected to a stirred turbulent state, which medium comprises at least one polyoxyalkylenated compound of the formula (V) and water in a quantity sufficient to initiate a phosphatization reaction, said medium being at an initial temperature of from about 35 to about 40° C., said temperature being maintained at less than or equal to about 45° C. until the introduction of phosphorus pentoxide is complete, the total quantity of said phosphorus pentoxide corresponding to a polyoxyethylenated compound:$P_2O_5$ ratio equal to 3±0.3:1, and
(2) maturing the resultant reaction mixture in a stirred turbulent state at a temperature of from about 40 to about 60° C.

5. The process of claim 4, wherein each $R_1$ is selected from the group consisting of tri(1-phenylethyl)phenyl, di(1-phenylethyl)phenyl, nonylphenyl, octylphenyl, docecylphenyl, tridecyl, octadecyl and octadecenyl radicals, and wherein each R and R' is selected from the group consisting of an ethylene and a propylene radical, and wherein each O—R and O—R' is from 3 to 60 oxyalkylenated units.

6. The process of claim 4, wherein said medium contains water in a quantity of from about 0.0025 to about 0.5 mole per mole of said polyoxyalkylenated compound or compounds of formula V.

7. A neutralized surfactant composition obtained by neutralizing the acid groups of a surfactant composition of claim 1.

8. The neutralized surfactant composition of claim 7, wherein said surfactant is neutralized using a base in a quantity sufficient to obtain a pH of at least 7, at a temperature not exceeding 60° C.

9. The neutralized surfactant composition of claim 8, wherein said base is an alkali metal hydroxide or an amine.

* * * * *